US00PP25866P3

(12) United States Plant Patent
Ferguson et al.

(10) Patent No.: US PP25,866 P3
(45) Date of Patent: Sep. 8, 2015

(54) STRAWBERRY PLANT NAMED 'DRISSTRAWTHIRTYSEVEN'

(50) Latin Name: *Fragaria×ananassa*
Varietal Denomination: DrisStrawThirtySeven

(71) Applicant: DRISCOLL STRAWBERRY ASSOCIATES, INC., Watsonville, CA (US)

(72) Inventors: Michael D. Ferguson, Moorpark, CA (US); Raquel Cervantes, Michoacan (MX); Jorge Rodriguez Alcazar, Texcoco (MX)

(73) Assignee: DRISCOLL STRAWBERRY ASSOCIATES, INC., Watsonville, CA (US)

( * ) Notice: Subject to any disclaimer, the term of this patent is extended or adjusted under 35 U.S.C. 154(b) by 96 days.

(21) Appl. No.: 13/998,836

(22) Filed: Dec. 13, 2013

(65) Prior Publication Data

US 2015/0173280 P1 Jun. 18, 2015

(51) Int. Cl.
*A01H 5/00* (2006.01)

(52) U.S. Cl.
USPC ..... Plt./208

(58) Field of Classification Search
USPC ..... Plt./208
See application file for complete search history.

*Primary Examiner* — Annette Para
(74) *Attorney, Agent, or Firm* — Jondle & Associates, P.C.

(57) ABSTRACT

A new and distinct variety of strawberry plant named 'DrisStrawThirtySeven' particularly characterized by a vigorous plant bearing medium red fruit having a mid-season harvest maturity is disclosed.

3 Drawing Sheets

Genus and species: *Fragaria×ananassa.*
Variety denomination: 'DrisStrawThirtySeven'.

BACKGROUND OF THE NEW PLANT

The present invention relates to a new and distinct strawberry variety designated 'DrisStrawThirtySeven' and botanically known as *Fragaria×ananassa.* This new strawberry variety was discovered in Ventura County, Calif. in February 2006 and originated from a cross between the proprietary female parent '18L33' (unpatented) and the proprietary male parent '10L297' (unpatented). A single plant was selected for asexual propagation via tissue culture and vegetative cuttings in Shasta County, Calif. in 2006.

'DrisStrawThirtySeven' underwent further testing in Zamora, Mexico for four years (2008-2012). The present invention has been found to retain its distinctive characteristics through successive asexual propagations via stolons and tissue culture.

Plant Breeder's Rights for this variety have not been applied for. 'DrisStrawThirtySeven' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Zamora, Mexico.

1. Vigorous plant;
2. Medium red fruit; and
3. Mid-season harvest maturity.

DESCRIPTION OF THE PHOTOGRAPHS

The accompanying color photographs show typical specimens of the new variety at various stages of development. The colors shown are as true as can be reasonably obtained by conventional photographic procedures. The photographs were taken from four-month-old plants.

DESCRIPTION OF THE NEW VARIETY

Figure 1:
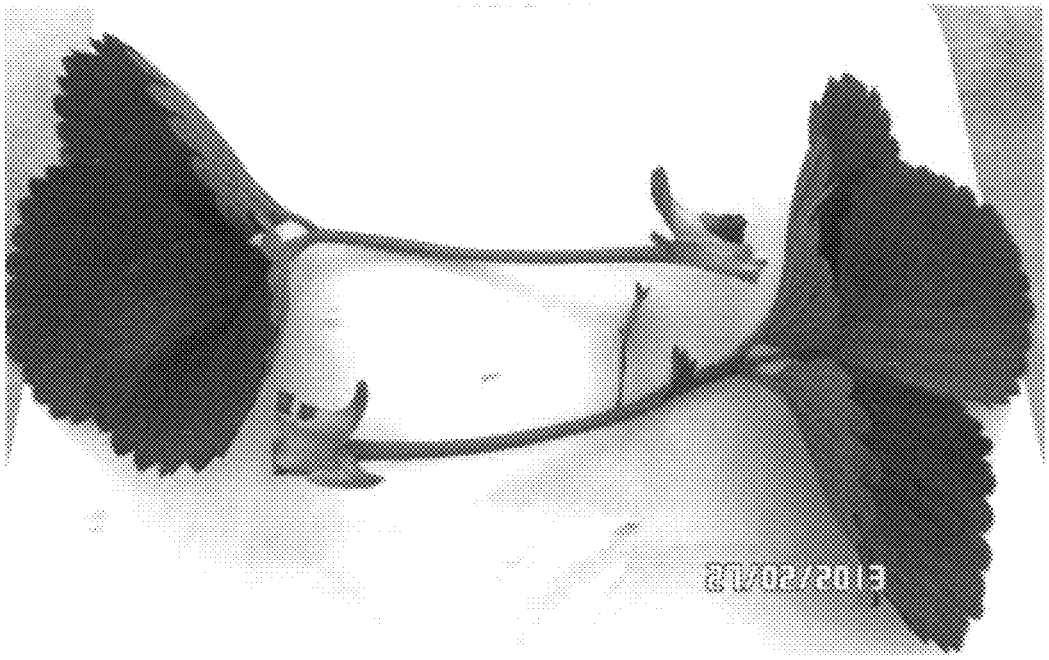
FIG. 1 shows upper and lower surfaces of the leaves of the plant with three leaflets.
Figure 2:
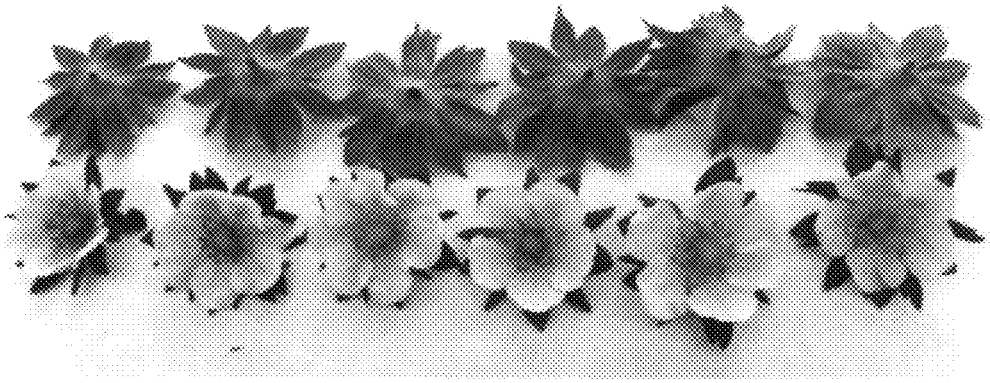
FIG. 2 shows both upper and lower surfaces of the flowers.
Figure 3:
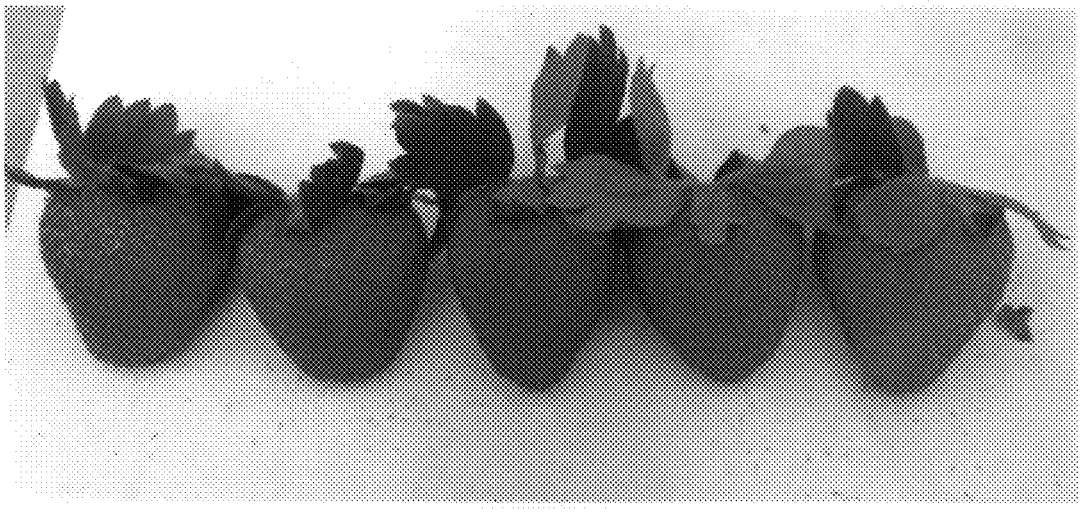
FIG. 3 shows the whole fruit.
Figure 4:
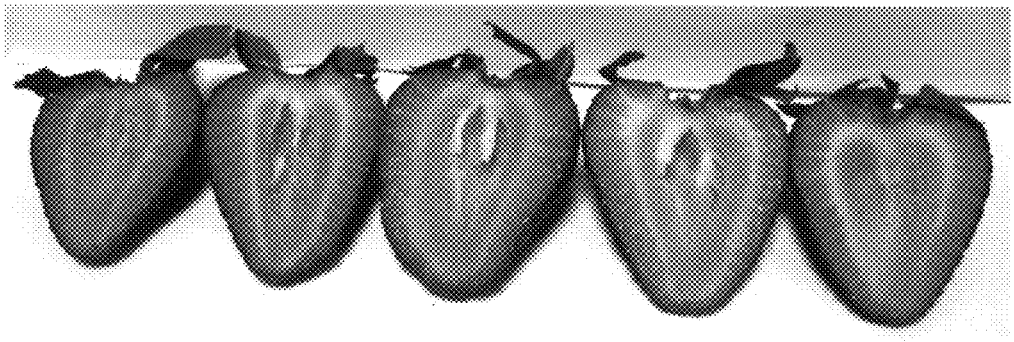
FIG. 4 shows the fruit in longitudinal cross-section.
Figure 5:
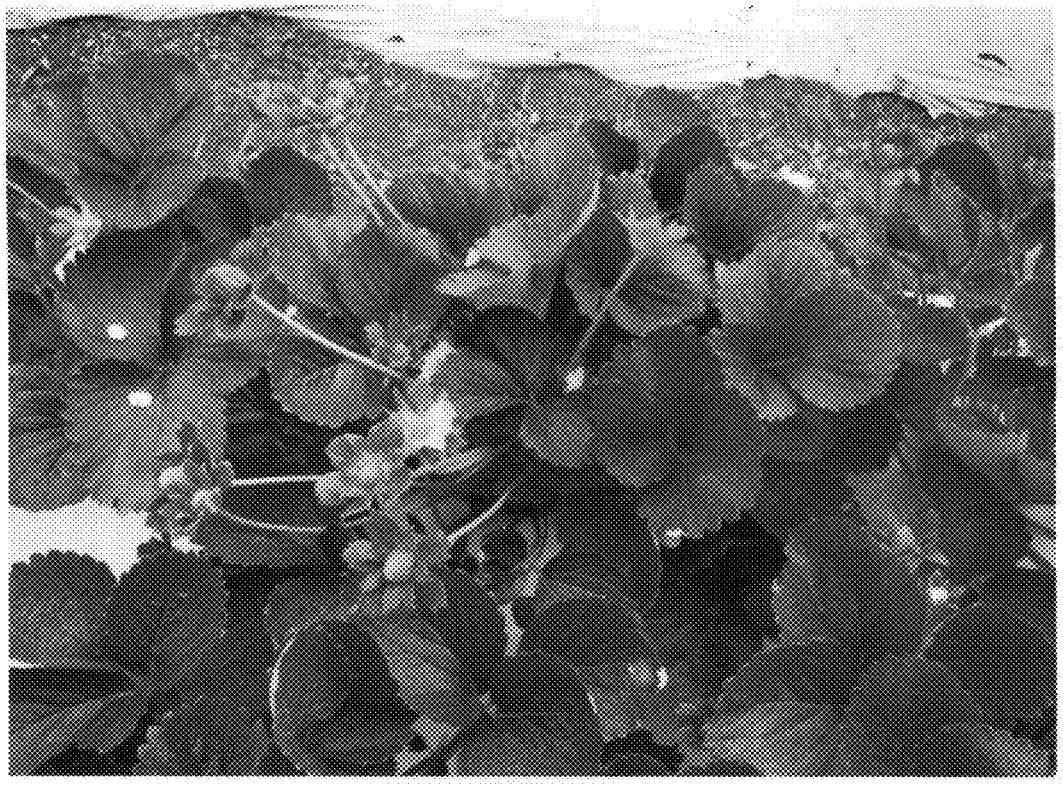
FIG. 5 shows the whole plant.

The following detailed descriptions set forth the distinctive characteristics of 'DrisStrawThirtySeven'. The data which define these characteristics is based on observations taken in Zamora, Mexico from 2008 to 2012. This description is in accordance with UPOV terminology. Color designations, color descriptions, and other phenotypical descriptions may deviate from the stated values and descriptions depending upon variation in environmental, seasonal, climatic, and cultural conditions. 'DrisStrawThirtySeven' has not been observed under all possible environmental conditions. The botanical description of 'DrisStrawThirtySeven' was taken from four-month-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* $2^{nd}$ edition by James G. Harris and Melinda Woolf Harris, unless where otherwise defined.

DETAILED BOTANICAL DESCRIPTION OF THE PLANT

Classification:

*Species.*—*Fragaria×ananassa.*
*Common name.*—Strawberry.
*Denomination.*—'DrisStrawThirtySeven'.

Parentage:
*Female parent.*—The proprietary variety '18L33' (unpatented).
*Male parent.*—The proprietary variety '10L297' (unpatented).
Plant:
*Height.*—18.5 cm.
*Diameter.*—27.2 cm.
*Number of crowns/plant.*—4.
*Habit.*—Flat globose.
*Density of individual plant.*—Medium.
*Vigor* (*health and hardiness of plant*).—Strong.
Terminal leaflets:
*Size.*—Medium. Length: 7.6 cm. Width: 7.5 cm. Length/width ratio: 1.0 (As long as broad).
*Number of teeth/terminal leaflet.*—20.
*Shape of teeth.*—Obtuse — serrate to crenate.
*Color.*—Upper surface: RHS 147A (Dark yellow-green). Lower surface: RHS 147C (Light yellow-green).
*Shape in cross section.*—Slightly convex.
*Blistering.*—Medium.
*Glossiness.*—Medium.
*Number of leaflets.*—Three only.
*Shape.*—Orbicular.
*Base shape.*—Rounded.
*Apex descriptor.*—Rounded.
*Variegation.*—Absent.
*Margin.*—Crenate.
*Margin profile.*—Involute (Margins rolled inwards).
Petiole:
*Length.*—Medium; 10.0 cm.
*Diameter.*—1.50 mm.
*Pubescence.*—Medium.
*Pose of hairs.*—Outwards — horizontal.
*Color.*—RHS 143C (Medium green).
*Bract frequency.*—2.
Petiolule:
*Length.*—6.59 mm.
*Diameter.*—0.62 mm.
*Color.*—RHS 143C (Medium green).
Stipule:
*Length.*—2.7 cm.
*Width.*—0.46 mm.
*Pubescence.*—Sparse.
*Stipule anthocyanin coloration.*—Absent or very weak; RHS 186A (Medium greyed-purple).
Inflorescence:
*Position relative to foliage.*—Beneath.
*Number of flowers.*—Medium.
*Time of flowering* (*50% of plants at first flower*).—Medium.
*Flower size.*—Medium.
*Diameter.*—26.33 mm.
*Petals.*—Shape: Orbicular. Apex: Rounded. Base: Concavo-convex. Margin: Entire. Spacing: Overlapping. Length: 13.88 mm. Width: 13.83 mm. Length/width ratio: 1.0 (As long as broad). Petal number per flower: 6 . Color (upper surface): RHS NN155D (White).
*Calyx.*—Diameter: 34.94 mm. Diameter relative to corolla: Larger. Inner calyx diameter relative to outer: Smaller. Insertion of calyx: In a basin — inserted. Pose of calyx segments: Spreading — outwards. Size of calyx in relation to fruit: Slightly larger. Adherence of calyx: Strong.
*Sepal.*—Shape: Ovate. Apex: Convex. Margin: Entire. Length: 16.19 mm. Width: 10.19 mm. Sepal number: 6.
*Receptacle color.*—RHS 145A (Medium yellow-green).
*Stamen.*—Present. Anther color: RHS 13A (Dark yellow).
*Pedicel.*—Attitude of hairs: Outwards — horizontal.
Fruiting truss:
*Length.*—Medium; 4.4 cm.
*Diameter at base of truss.*—36.9 mm.
*Number of berries per fruiting truss.*—1.
*Attitude at first picking.*—Semi-erect.
*Color at base of truss.*—RHS 144C (Medium yellow-green).
Fruit:
*Relative fruit size.*—Medium.
*Length.*—38.39 mm.
*Width.*—32.19 mm.
*Length/width ratio.*—1.2 (Longer than broad).
*Fruit weight.*—32.6 g.
*Fruit hollow length.*—4.698 mm.
*Fruit hollow width.*—3.924 mm.
*Fruit hollow length/width ratio.*—1.2 (Longer than broad).
*Fruit hollow center* (*cavity*).—Large.
*Predominant fruit shape.*—Conical.
*Difference in shape between primary and secondary fruits.*—Slight.
*Evenness of fruit surface.*—Even or very slightly uneven.
*Fruit skin color.*—RHS 46A (Dark red).
*Evenness of fruit color.*—Slightly uneven.
*Fruit glossiness.*—Medium.
*Achenes.*—Insertion of achenes: Level. Coloration (sunward side of berry): RHS 150C (Light yellow-green). Coloration (shaded side of berry): RHS 145C (Light yellow-green). Number per berry: 346. Weight (weight of achenes divided by total # seed): 0.000319 g. Width of band without achenes: Absent or very narrow.
*Firmness of flesh* (*when fully ripe*).—Firm.
*Color of flesh* (*excluding core*).—RHS 45B (Medium red).
*Color of core.*—RHS 42B (Light red).
*Evenness of flesh color.*—Slightly uneven.
*Distribution of flesh color.*—Marginal and central.
*Sweetness.*—Medium.
*Acidity.*—Medium.
*Texture when tasted.*—Medium.
*Type of bearing.*—Not everbearing — not remontant.
*Harvest interval.*—Early November-late April.
*Harvest maturity.*—Mid-season.
*Production per plant.*—506.9 g.
Disease and pest resistance:
*Tetranychus urticae.*—Moderately resistant.
*Lygus hesperus* (*Lygus* bug).—Moderately resistant.
*Botrytis fruit rot.*—Moderately resistant.
*Powdery mildew.*—Moderately resistant.
*Xanthomonas fragariae.*—Moderately resistant.

COMPARISON WITH PARENTAL AND COMMERCIAL VARIETIES

When 'DrisStrawThirtySeven' is compared to the female parent '18L33' (unpatented), 'DrisStrawThirtySeven' has lighter colored, firmer fruit with a better conic shape and an earlier fruit production season than '18L33'.

When 'DrisStrawThirtySeven' is compared to the male parent '10L297' (unpatented), 'DrisStrawThirtySeven' has more vigorous and larger plants and higher fruit production with better flavor and softer fruit than '10L297'.

When 'DrisStrawThirtySeven' is compared to the commercial variety 'Driscoll El Dorado' (U.S. Plant Pat. No. 16,238), 'DrisStrawThirtySeven' has leaves with medium interveinal blistering that are slightly convex in cross section and have an involute terminal leaflet margin profile, whereas 'Driscoll El Dorado' has leaves with weak interveinal blistering that are slightly concave in cross section and have a revolute to flat terminal leaflet margin profile. Additionally, 'DrisStrawThirtySeven' has medium glossy fruit with a large hollow center and achenes that are inserted level with the surface, whereas 'Driscoll El Dorado' has strongly glossy fruit with a medium hollow center and achenes that are inserted below the surface.

When 'DrisStrawThirtySeven' is compared to the commercial variety 'DrisStrawTwenty' (U.S. Plant Pat. No. 23,383), 'DrisStrawThirtySeven' has a flat globose habit with an average of 4 crowns per plant, whereas 'DrisStrawTwenty' has a globose to semi-upright habit with an average of 3 crowns per plant. Additionally, 'DrisStrawThirtySeven' has medium sized, medium glossy fruit with a large hollow center, whereas 'DrisStrawTwenty' has large, strongly glossy fruit with a medium hollow center.

We claim:

1. A new and distinct variety of strawberry plant named 'DrisStrawThirtySeven' as described and shown herein.

* * * * *